United States Patent [19]

Hideg et al.

[11] Patent Number: 4,731,376
[45] Date of Patent: Mar. 15, 1988

[54] 2-(-(2,2,5,5-TETRAMETHYL-3-PYRROLIN-3-CARBONYL))-AMINO DERIVATIVES

[75] Inventors: Kálmán Hideg; Olga H. Hankovszky, both of Pécs; László Frank, Tiszavasvári; Ilona Bódi, Tiszavasvári; József Csák, Tiszavasvári, all of Hungary

[73] Assignee: Alkaloida Vegyeszeti Gyar, Tiszavasvári, Hungary

[21] Appl. No.: 898,723

[22] PCT Filed: Jan. 20, 1984

[86] PCT No.: PCT/HU84/00004

§ 371 Date: Sep. 20, 1984

§ 102(e) Date: Sep. 20, 1984

[87] PCT Pub. No.: WO84/02906

PCT Pub. Date: Aug. 2, 1984

Related U.S. Application Data

[63] Continuation of Ser. No. 662,299, Sep. 20, 1984, abandoned.

[30] Foreign Application Priority Data

Jan. 20, 1983 [HU] Hungary ............... 178/83

[51] Int. Cl.[4] ............ A61K 31/40; A61K 31/44; C07D 207/09; C07D 207/18
[52] U.S. Cl. ............ 514/423; 514/343; 546/281; 548/537
[58] Field of Search ............ 548/537; 514/423, 343; 546/281

[56] References Cited

U.S. PATENT DOCUMENTS 3,020,288  2/1962  Wragg et al. ............ 548/537 X
3,334,103  8/1967  Feldman et al. ............ 548/537 X
4,111,901  9/1978  Hechenbleikner ............ 548/537 X

FOREIGN PATENT DOCUMENTS 109345  3/1900  Fed. Rep. of Germany ...... 548/537
109346  3/1900  Fed. Rep. of Germany ...... 548/537
109347  3/1900  Fed. Rep. of Germany ...... 548/537
　4799  1/1900  United Kingdom ............ 548/537

Primary Examiner—Joseph Paul Brust
Attorney, Agent, or Firm—Karl F. Ross; Herbert Dubno; Jonathan Myers

[57] ABSTRACT

Compounds are disclosed of the formula (I)

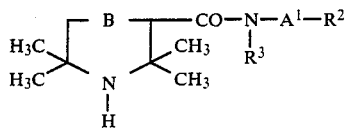

wherein
$A^1$ is a valence bond or a $C_1$ to $C_5$ straight or branched chain alkylene group unsubstituted or substituted by hydroxy or aminocarbonyl;
B is a valence bond or a double bond;
$R^3$ is hydrogen or $C_1$ to $C_4$ alkyl;
$R^2$ is a phenyl or phenoxy group unsubstituted or substituted by one or two $C_1$ to $C_4$ alkyl groups, $C_1$ to $C_4$ alkoxy groups, or halo substituents; or $R^2$ is an amino group, a diphenylmethyl group, or an $R^4$ —NH—CO— group in which
$R^4$ is 2,6-dimethyl-phenyl; or a pharmaceutically acceptable acid addition salt thereof. The compounds possess anti-arrhythmic activity and exert little or no hypotensive side effects.

18 Claims, No Drawings

2-(-(2,2,5,5-TETRAMETHYL-3-PYRROLIN-3-CARBONYL))-AMINO DERIVATIVES

This is a continuation of application Ser. No. 662,299, filed Sept. 20, 1984 and now abandoned.

The invention relates to new chemical compounds, methods for making same and pharmaceutical media which contain these compounds.

Subject of the invention are compounds of the general formula I

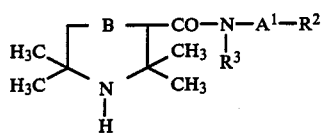

where $A^1$ is a valence bond, a straight or branched alkylene group having 1 to 5 carbon atoms which can be substituted with a hydroxyl- or amino-carbonyl group, B represents a single or a double bond, $R^2$ represents an aromatic, heteroaromatic or aryloxy group which can be substituted with one or more alkyl- or alkoxy group containing 1 to 4 carbon atoms or with halogen atoms, or an amino group or a diphenyl-methyl group, or a $R^4$—NH—CO group, in which $R^4$ is an aromatic group possibly substituted with an alkyl group, advantageously a phenyl group, $R^3$ is hydrogen or an alkyl group containing 1 to 4 carbon atoms.

In this description the significance of the substituents in the general formulae is also as follows:

$B^1$ a single or a double bond

A is an alkylene group with 1 to 4 carbon atoms which possibly can be substituted with a hydroxyl group.

Since the above representations do not change, we refrain from repeating them.

The new compounds of the invention can be used as the basis for pharmaceutical media. They can also be used as intermediates in the chemical production of medically effective materials, especially for antiarrhythmics.

Our research upon different models has shown that the compounds of the general formula I and their salts have significant antiarrhythmic characteristics, so that the compounds under biological conditions function as heart rhythm disturbance amelioraters. The effectivity can be compared advantageously with pharmaceuticals acceptable in therapy (Chinidin, Lydocain, procainamide) and in many cases exceeds the effect of these pharmaceuticals.

A further advantage of the compounds according to the invention is that in the effective range of antiarrhythmic dosage, they do not generate arrhythmia of the heart chamber, do not produce bradycardia and do not reduce the blood pressure in animal subjects or only reduce the blood pressure in animal subjects to a minimum extent.

With parenteral and enteral administration, the compounds of the general formula I or their salts can be used advantageously against disturbances of heart rhythm as a prophylactic and as also a treatment.

Below, the pharmacological effect of the compounds of the general formula I is demonstrated on an aconitin arrhythmia model on rats (Zetler and Strubelt, Arzenim-Forsch. (Drug Res.) 30, 1497, 1980).

Wistar rats (200–220 g) are narcotized with urethane. The vena jugularis is connected with a polyethylene catheter. Using standard EKG-II leads, a control EKG is taken. The test substance and the physiological saline solution used as control are intravenously administered 5 minutes before the aconitin infusion. The aconitin solution is continuous administered at a dose of 5 mg/kg at a rate of 0.1 ml (100 g/minute) as an infusion into the vena jugularis. The progress is monitored by the EKG isoelectric line.

During the test the time to formation of the ventricular extrasystole, ventricular tachycardia and fibrillation were determined. Several results, each for a different type of compound, are collected in table II.

On the basis of the late occurrence of the ventricula extrasystole, $ED_{125}$ and $ED_{150}$ values were determined. The acute toxicities were determined on mice (CELP strain and the $LD_{50}$ value was calculated after a week using the Litchfield-Wilcoxon method. The antiarrhythmically effective dosage or the $LD_{50}$ value for several compounds of the various compound types are collected in Table III.

The compounds of the invention can be worked up with known methods for direct use as pharmaceuticals utilizing known methods of the pharmaceutical industry. Diluents, carriers and other auxiliary agents can be added. The pharmaceuticals can be put up in the form of tablets, dragees, capsules or like peroral formulations. The pharmaceutical can also be dispensed in parenteral form, mainly as i.v. injections. Body tissue is not attacked by the active ingredient.

The compounds of formula I can advantageously be used in the form of physiologically neutral or advantageous salts. For this purpose it is advantageous to use the hydrogen chloride, sulfuric acid or sulfonic acid salts or salts formed with hydrogen bromide.

From a biological view point, certain compounds are preferred, these being those in which the substituent-$A^1$-$R^2$ is represented by a substituted amino-carbonyl group. Under this class of compounds are compounds which can be substituted in the amino group with a variously substituted aromatic ring. These compounds show a superior antiarrhythmic effect and also other advantageous heart effects. These are for example ortho and/or parasubstituted alkyl-phenyl derivatives. One can also use such derivatives and have alkoxy or halogen substitutions. Advantageous substituents are for example methyl, ethyl, isopropyl, methoxy, ethoxy, chlorine, bromine etc.

Compounds of the general formula V constitute a subgroup of the general formula I; they, first of all, are valuable as intermediates in the form of other pharmaceutically effective agents. Thus, for example, it can be advantageous to provide various substituted derivatives of the primary amino group and may be made by prior or subsequent reduction of the pyrroline ring reacted with oxo compounds.

The compounds of the Formula (V) have the following formula:

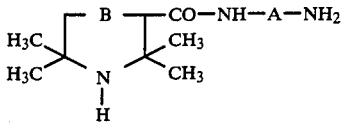 (V)

The subject of the invention is also the chemical production of the compounds of the general formula I. For this purpose, 2,2,6,6-tetra-methyl-3,5-dibromopiperidin-4-on compounds of the general formula III can be reacted. Then, preferably the resulting carboxamide with the general formula IV, can be reduced to saturate the pyrroline ring and/or the compound can be transformed into a salt with an inorganic or organic acid.

The compound of the Formula (II) has the following formula:

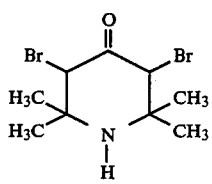 (II)

The compound of the Formula (III) has the following formula:

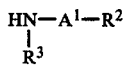 (III)

and the compound of the Formula (IV) has the following formula:

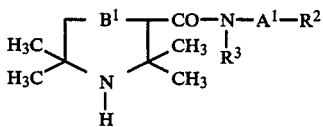 (IV)

It is known from the literature that one can produce different aminoalkyl substituted carboxamides from the dibromo derivatives of the formula II (Golding, Ioannou, O'Brien; Synthesis, 1975, 462).

The compounds of formula II are advantageously reacted with aqueous solutions of compounds of the general formula III. It is advantageous to isolate the resulting precipitate by extraction with a water-insoluble solvent.

The reaction is generally carried out at room temperature; it can, however, also be carried out at higher temperatures.

As starting materials one can also use a salt of the piperidine base. In this case the use of the hydrogen bromide salt is advantageous.

As water-insoluble solvent, it is preferred to use halogenated hydrocarbons such as chloroform. The reaction can be carried out in the presence of an organic or inorganic base.

To work up the reaction mixture the following procedure is preferably used:

The solution in a water-insoluble solvent is dried over sodium sulfate or magnesium sulfate, whereupon the solvent and possibly excess diamine are driven off. The product is then crystallized from the residue. The crystallization can be accelerated by the addition of a solvent such as chloroform and/or ether.

For producing the compounds of the general formula VII, the pyrroline derivatives of the Formulae (I), (IV) or (V), made as described above, are subjected to a reduction.

The compound of the Formula (VII) has the formula:

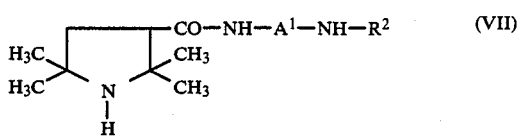 (VII)

The compounds of the Formula (V) are produced by reacting a compound of the Formula (II) in the form of a base or of a salt with a compound of the Formula (VI):

 (VI)

The reduction is advantageously carried out by a catalytic hydrogenation, preferably in the presence of a palladium-carbon catalyst. The hydrogenation is effected preferably at atmospheric pressure in the presence of an organic solvent. As organic solvent one can advantageously use water-insoluble organic solvents such as chloroform.

The working up of the reaction mixture is effected after removal of the catalyst by extraction and concentration of the extract.

The compounds of the general formula I can also be used as intermediates for further synthesis. For this purpose the isolation of the product from the reaction mixture in many cases is not necessary.

Compounds of the general formula I in which B for an individual compound is optically active can thus appear in the dextro-rotary or levo-rotary form. Within the protection of this patent are both optically active forms as well as their racemates.

Further details of the invention are found in the examples.

EXAMPLE 1

4.31 g of 2-amino-3-(2,6-dimethyl-phenoxy)-propane hydrogen chloride are dissolved in 60 ml of ethanol and diluted with 20 ml of water. After addition of 8.3 g of potassium carbonate, 7.88 g of 3,5-dibromo-2,2,6,6-tetramethyl-4-piperidone hydrogen bromide is added at room temperature in portions. After 3 hours, the solution is saturated with about 120 g of potassium carbonate and is extracted four times with 20 ml of chloroform for each extraction. The extract is washed with water, dried over magnesium sulfate and filtered. The filtrate is evaporated to dryness, whereupon the residue is dissolved in 30 ml of ether and diluted with 40 ml of n-hexane. The separated precipitate is filtered cold and dried. 5.24 g (82%) 2-[N(2,2,5,5-tetramethyl-2,5-dihydro-3-pyrroline-3-carbonyl)]-3-(2,6-dimethyl-phenoxy)-aminopropane are obtained (see compound No. 9 in table I).

The compounds Nos. 1–10 of table I are produced from the corresponding amines as above. The data is given in the table.

EXAMPLE 2

3.29 g of the product produced in Example 1 are dissolved in 20 ml of chloroform and treated with hydrogen in the presence of a high activity palladium/carbon catalyst until takeup ceases. The resulting solution is filtered and concentrated and worked up as described in Example 1. The product is 2-[N-(2,2,5,5-tetramethyl-3-pyrrolidine-3-carbonyl)]-3-(2,6-dimethyl-phenoxy)-amino propane (compound No. 11 in Table I).

EXAMPLE 3-4-5

31.30 g of 2,2,6,6-tetramethyl-3,5-dibromo-piperid-4-on are formed into solution as follows and each is cooled to 0° C.:

(a) a solution of 27.04 g of 1,3-diamino-2-propanol in 500 ml of water, (b) a solution of 9.01 g of 1,3-diamino-2-propanol and 20.20 g of triethylamine in 500 ml of water, and (c) a solution of 9.01 g of 1,3-diamino-2-propanol and 13.82 g of potassium carbonate in 500 ml of water.

Each reaction mixture is stirred for an additional hour at 0° C. Then sufficient potassium carbonate (approximately 200 g) is added until the product appears as an upper phase above the surface of the aqueous phase. After extraction with chloroform (3×100 ml) the chloroform solution is dried over magnesium sulfate. The solvent and any excess of amine is driven off at reduced pressure. The residue is dissolved in 150 ml of ether. The separated N-(2-hydroxy-3-amino-propyl)-2,2,5,5-tetramethyl-3-pyrroline-3-carboxamide is filtered in crystalline form, washed and dried (compound No. 15 in table I).

EXAMPLES 6-7-8

39.39 g of the hydrogen bromide acid salt of 2,2,6,6-tetramethyl-3,5-dibromo-piperid-4-on its introduced into each of the following solutions which is then cooled to 0° C.:

(a) a solution of 36.05 g 1,3-diamino-2-propanol in 500 ml of water, or (b) a solution of 9.01 g 1,3 diamino-2-propanol and 3.03 g triethylamine in 500 ml of water, and (c) a solution of 9.01 g 1,3-diamino-2-propanol and 20.73 g potassium carbonate in 500 ml of water.

One works as in Examples 3-4-5. The resulting products correspond to the products of Examples 3-4-5 (compound No. 15 in table I).

EXAMPLE 9

22,53 g N-(3-amino-propyl)-2,2,5,5-tetramethyl-3-pyrolline-3-carboxamide (compound No. 13 in table I) is dissolved in 300 ml of chloroform and reacted in the presence of palladium on carbon catalyst of high activity with hydrogen until hydrogen takeup terminates. The reaction mixture is worked up as described in Example 1. The resulting oily product can be used directly for further synthesis. The product is N-(3-amino-propyl)-2,2,5,5-tetramethyl-pyrrolidine-3-carboxamide (compound No. 18 in table I).

TABLE I $$R^1-CON-A^1-R^3$$
$$\phantom{R^1-CON-A^1-}R^3$$

| No | R¹ | R² | A¹ | R³ | Yield % | mp, °C. | Molecular formula (M.w.) | Analysis, % calcd/found C | H | N | Cl | ¹H-nmr, 60 MHz, δ relative to SiMe₄ |
|---|---|---|---|---|---|---|---|---|---|---|---|---|
| 1 | 2,2,5,5-tetramethyl-2,5-dihydro-1H-pyrrol-3-yl | phenyl | —CH₂— | H | 68 | 188–189 | C₁₆H₂₂N₂O.HCl (294.82) | 65.18 / 65.17 | 7.86 / 6.12 | 9.50 / 9.58 | 12.02 / 12.22 | 1.50(s,6H,2CH₃); 1.60(s,6H,2CH₃); 4.30(s,2H,CH₂); 6.22(s,1H,CH=); 7.20(s,5H,ArCH=)(D₂O) |
| 2 | 2,2,5,5-tetramethyl-2,5-dihydro-1H-pyrrol-3-yl | 4-chlorophenyl | —CH₂— | H | 71 | 216–218 | C₁₆H₂₁ClN₂O.HCl (329.28) | 58.36 / 58.40 | 6.74 / 7.00 | 8.51 / 8.52 | 21.53 / 21.67 | 1.52(s,6H,2CH₃); 1.62(s,6H,2CH₃); 4.26(s,2H,CH₂); 6.28(s,1H,CH=); 7.14(s,4H,ArCH=)(D₂O) |
| 3 | 2,2,5,5-tetramethyl-2,5-dihydro-1H-pyrrol-3-yl | 4-methoxyphenyl | —CH₂— | H | 69 | 82–83 | C₁₇H₂₄N₂O₂ (288.39) | 70.80 / 70.99 | 8.39 / 8.34 | 9.71 / 9.46 | — / — | 1.24(s,6H,2CH₃); 1.44(s,6H,2CH₃); 3.65 (s,3H,OCH₃); 4.37(s,2H,CH₂); 6.02(s, 1H,CH=); 6.70–7.30(m,4H,ArCH=),(D₂O) |
| 4 | 2,2,5,5-tetramethyl-2,5-dihydro-1H-pyrrol-3-yl | phenyl | —CH₂— | CH₃ | 50 | 214–216 | C₁₇H₂₄N₂O₂.HCl (324.85) | 62.86 / 62.62 | 7.76 / 7.86 | 8.62 / 8.58 | 10.91 / 10.75 | 1.52(s,6H,2CH₃); 1.62(s,6H,2CH₃); 3.66(s,3H,OCH₃); 4.24(s,2H,CH₂); 6.22(s,1H,CH=); 6.70–7.80(m,4H, ArCH=)(D₂O). |
| 5 | 2,2,5,5-tetramethyl-2,5-dihydro-1H-pyrrol-3-yl | phenyl | —CH— CONH₂ | H | 93 | 225–226 | C₁₇H₂₄N₂O.HCl (308.87) | 66.11 / 66.16 | 8.16 / 8.27 | 9.07 / 9.06 | 11.48 / 11.52 | 1.52(s,6H,2CH₃); 1.60(s,6H,2CH₃); 2.90(s,3H,NCH₃); 4.58(s,2H,CH₂); 6.04(s,1H,CH=);7.10–7.60(m,5H, ArCH=)(DMSO). |
|   | 2,2,5,5-tetramethyl-2,5-dihydro-1H-pyrrol-3-yl | phenyl |   |   |   | 220–221 | C₁₇H₂₃N₃O₂ (301.39) | 67.75 / 67.59 | 7.69 / 7.71 | 13.94 / 13.61 | — | 1.30(s,6H,2CH₃); 1.40(s,6H,2CH₃); 5.62(s,1H,CH); 6.22(s,1H,CH=); 7.30–7.45(m,5H,ArCH=)(CDCl₃). |
|   |   |   |   |   |   | 220–223 | C₁₇H₂₃N₃O₂.HCl (337.87) | 60.44 / 60.43 | 7.16 / 7.25 | 12.44 / 12.43 | 10.49 / 10.43 | 1.52(s),1.54(s),1.60(s),1.66(s), (12H,4CH₃); 5.40(s,1H,CH); 6.40(s,1H, CH=); 7.36(s,5H,ArCH=),(D₂O) |

TABLE I-continued

| # | Structure 1 | Linker | Structure 2 | R | Yield | mp | Formula (MW) | Analysis | NMR |
|---|---|---|---|---|---|---|---|---|---|
| 6 | Me₂C=CH-CMe₂-NH (pyrrolidine) | -CH- with Ph | phenyl | H | 97 | 170-171 | C₂₂H₂₆N₂O (334.46) | 79.00 7.84 8.38 / 79.20 7.67 8.51 | — | 1.26(s,6H,2CH₃); 1.42(s,6H,2CH₃); 6.08(s,1H,CH); 6.24(s,1H,CH=); 7.26(s,10H,ArCH=)(CDCl₃). |
| 7 | Me₂C=CH-CMe₂-NH | -CH₂-CH₂- | 3,4-dimethoxyphenyl | | | 245-247 | C₂₂H₂₆N₂O.HCl (370.92) | 71.24 7.34 7.55 9.56 / 70.98 7.31 7.35 9.86 | 1.52(s,6H,2CH₃); 1.60(s,6H,2CH₃); 6.10(s,1H,CH); 6.30(s,1H,CH); 7.29(s,10H,ArCH=)(D₂O). |
| 8 | Me₂C=CH-CMe₂-NH | -CH₂- | 4-pyridyl | H | 45 | 212-214 | C₁₉H₂₈N₂O₃.HCl (368.92) | 61.86 7.92 7.59 9.61 / 61.76 8.03 7.61 9.86 | 1.52(s,12H,4CH₃); 2.50-2.85(m,2H,CH₂); 3.25-3.65(m,2H,CH₂); 3.76(s,6H,2OCH₃); 6.05(s,1H,CH=); 6.70-7.0(m,3H,ArCH=)(D₂O). |
| 9 | Me₂C=CH-CMe₂-NH | -CH-CH₃ | 2,6-dimethylphenoxy | H | 68 | 198-200 | C₁₅H₂₁N₃O.2HCl (332.29) | 54.22 6.98 12.65 21.34 / 54.37 7.09 12.49 21.48 | 1.60(s,6H,2CH₃); 1.66(s,6H,2CH₃); 4.70(s,2H,CH₂); 6.58(s,1H,CH=); 7.80-8.05(m,2H,PyCH=); 8.60-8.80(m,2H,PyCH=)(D₂O). |
| | | | | H | 82 | 134-135 | C₂₀H₃₀N₂O₂ (330.47) | 72.69 9.15 8.48 / 72.87 8.92 8.44 | — | 1.28(s,2CH₃), 1.45(s,2CH₃), 1.43(d,CH₃)(15H); 2.24(s,6H,2CH₃); 3.50-4.0(m,2H,CH₂); 4.0-4.50(m,1H,CH); 6.08(s,1H,CH=); 6.84(s,3H,ArCH=)(CDCl₃). |
| | | | | H | | 218 (dec.) | C₂₀H₃₀N₂O₂.HCl (366.93) | 65.47 8.52 7.63 9.66 / 65.41 8.32 7.68 9.82 | 1.24(d,3H,CH₃); 1.58(s,6H,2CH₃); 1.68(s,6H,2CH₃); 2.14(s,6H,2CH₃); 3.55-3.80(m,2H,CH₂); 3.95-4.30(m,1H,CH); 6.24(s,1H,CH=); 6.90(s,3H,ArCH=)(D₂O). |
| 10 | Me₂C=CH-CMe₂ | — | -NH-Ph | H | 52 | 238-239 | C₁₅H₂₁N₃O.HCl (295.82) | 60.91 7.50 14.20 11.98 / 61.06 7.34 14.21 12.05 | 1.68(s,6H,2CH₃); 1.66(s,6H,2CH₃); 6.46(s,1H,CH=); 6.70-7.50(m,5H,ArCH=)(D₂O). |

TABLE I-continued

| 1 | 2 | 3 | 4 | 5 | 6 | 7 | 8 | | | 9 |
|---|---|---|---|---|---|---|---|---|---|---|
| 11 | ![structure](Me2C-NH-CMe2 pyrrolidine) | -CH—CH2—<br>　\|<br>　CH3 ...H3C-phenyl-OCH3 with H3C | H | 50 | 216-218 | C20H32N2O2·HCl<br>(368.94) | 65.11<br>64.98 | 9.02<br>9.13 | 7.59<br>7.65 | 9.61<br>9.83 | 1.0–1.80(m,15H,4CH3,CH2CH); 1.80–2.40(m,9H,3CH3);3.20–3.65(m, 2H,CH2); 2.70–3.80(m,3H,CHCH2); 6.68(s,3H,ArCH=)(D2O). |
| 12 | ![pyrroline Me2C=CMe2 NH] | -CH2CH2-NH2 | H | 70 | 115-117 | C11H21N3O<br>(211.32) | 62.53<br>62.64 | 10.02<br>10.14 | 19.89<br>19.88 | — | 1.26(s,6H,2CH3); 1.34(s,6H,2CH3); 2.70–3.05(m,2H,CH2);3.20–3.65(m, 2H,CH2); 6.10(s,1H,CH=)(CDCl3). |
| 13 | ![pyrroline] | -CH2CH2CH2-NH2 | H | 70 | 87-88 | C12H23N3O<br>(225.35) | 63.97<br>64.06 | 10.29<br>10.33 | 18.65<br>18.72 | — | 1.28(s,6H,2CH3); 1.42(s,6H,2CH3); 1.50–1.95(m,2H,CH2); 2.70–3.20(m, 2H,CH2); 3.24–3.65(m,2H,CH2); 6.10 (s,1H,CH=)(CDCl3). |
| 14 | ![pyrroline] | -CH2-CH-NH2<br>　　\|<br>　　CH3 | H | 50 | 93-95 | C12H23N3O<br>(225.36) | 63.96<br>63.89 | 10.29<br>10.32 | 18.65<br>18.69 | — | 1.12(d,3H,CH3); 1.30(s,6H,2CH3); 1.45(s,6H,2CH3); 2.70–3.65(m,3H, CH2CH); 6.10(s,1H,CH=)(CDCl3). |
| 15 | ![pyrroline] | -CH2CH—CH2—NH2<br>　　　\|<br>　　　OH | H | 68 | 83-85 | C12H23N3O2<br>(241.35) | 69.72<br>69.66 | 9.61<br>9.69 | 17.41<br>17.44 | — | 1.28(s,6H,2CH3); 1.42(s,6H,2CH3); 2.50–2.85(m,2H,CH2); 3.20–3.94(m, 3H,CH2CH); 6.10(s,1H,CH=)(CDCl3); |
| 16 | ![pyrroline] | -CH2CH2CH2CH2NH2 | H | 55 | 108-111 | C13H25N3O<br>(239.38) | 65.23<br>65.32 | 10.53<br>10.60 | 17.55<br>17.57 | — | 1.28(s,6H,2CH3); 1.42(s,6H,2CH3); 1.24–2.05(m,4H,2CH2); 3.10–3.55(m, 4H,2CH2); 6.14(s,1H,CH=)(CDCl3). |
| 17 | ![pyrroline] | 　　CH3<br>　　\|<br>-CH2-C-NH2<br>　　\|<br>　　CH3 | H | 60 | 108-110 | C13H25N3O<br>(239.38) | 65.23<br>65.30 | 10.53<br>10.61 | 17.55<br>17.51 | — | 1.18(s,6H,2CH3); 1.32(m,6H,2CH3); 1.50(s,6H,2CH3); 3.16(d,2H,CH2; 6.14(s,1H,CH=)(CDCl3). |

TABLE I-continued

| # | Structure | R | Yield | mp | Formula (MW) | C found/calc | H | N | NMR |
|---|---|---|---|---|---|---|---|---|---|
| 18 | Me-Me / Me-Me ring N-H | —CH$_2$CH$_2$CH$_2$—NH$_2$ | H | 76 | olaj | C$_{12}$H$_{25}$N$_3$O (227.36) | 63.40 / 63.56 | 11.08 / 11.19 | 18.48 / 18.36 | — | 0.95–1.45(m,12H,4CH$_3$); 1.45–2.20 (m,5H,CH$_2$CH,CH$_2$); 2.52–3.05(m,2H, CH$_2$); 3.10–3.45(m,2H,CH$_2$)(CDCl$_3$). |
| 19 | Me-Me / Me-Me ring N-H (with =) | —CH$_2$—C(=O)—NH-(2,6-diMe-Ph) | H | 63 | 211–213 | C$_{19}$H$_{27}$N$_3$O$_2$·HCl (365.90) | 63.37 / 63.18 | 7.71 / 7.91 | 11.48 / 11.49 | 9.69 / 9.72 | 1.57(s,6H,2CH$_3$); 1.66(s,6H,2CH$_3$); 2.10(s,6H,2CH$_3$); 4.10(s,2H,CH$_2$); 6.45(s,1H,CH=); 7.10(s,3H,ArCH=) (D$_2$O) |
| 20 | Me-Me / Me-Me ring N-H (with =) | —CH(CH$_3$)—C(=O)—NH-(2,6-diMe-Ph) | H | 59 | 187–188 | C$_{20}$H$_{29}$N$_3$O$_2$ (343.47) | 69.94 / 69.90 | 8.51 / 8.29 | 12.23 / 12.29 | — | 1.26(s,6H,2CH$_3$); 1.31(s,6H,2CH$_3$); 1.52(d,3H;CH$_3$,J=7.2Hz); 2.15(s, 6H,2CH$_3$); 4.86(q,1H,CH,J=7.2Hz); 6.20(s,1H,CH=); 7.0(s,3H,ArCH=) (CDCl$_3$) |
|  |  |  |  |  | 168–169 | C$_{20}$H$_{29}$N$_3$O$_2$·HCl (379.93) | 63.23 / 63.37 | 7.96 / 7.65 | 11.06 / 10.92 | 9.33 / 9.34 | 1.52(d),1.54(s),1.62(s)(15H, 5CH$_3$); 2.10(s,6H,2CH$_3$); 4.40–4.80 (m,1H,D$_2$O alatt); 6.44(s,1H,CH=); 7.10(s,3H,ArCH=) (D$_2$O) |
| 21 | Me-Me / Me-Me ring N-H (with =) | 2,6-dimethylphenyl | H | 50 | 127–129 | C$_{17}$H$_{24}$N$_2$O (272.41) | 74.96 / 75.06 | 8.88 / 8.97 | 10.28 / 10.35 | — | 1.38(s,6H,2CH$_3$); 1.52(s,6H,2CH$_3$); 2.24(s,6H,2CH$_3$); 6.22(s,1H,CH=); 7.08(s,3H,ArCH=)(CDCl$_3$) |
|  |  |  |  |  | 195–199 | C$_{17}$H$_{24}$N$_2$O·HCl (308.87) | 66.11 / 66.23 | 8.16 / 8.36 | 9.07 / 9.22 | 11.48 / 11.63 | 1.75(s,6H,2CH$_3$); 1.85(s,6H,2CH$_3$); 2.28(s,6H,2CH$_3$); 6.66(s,1H,CH=); 7.24(s,3H,ArCH=)(D$_2$O) |

TABLE II

Changes of the appearance times of EKG changes (in rats) resulting from an aconitin infusion (minutes; X ± S.E.M.) n = number of test animals.

| Compound No. | Dosage mg/kg i.v. | n | Chamber extrasystol min. ± S.E.M. | Chamber tachycardia min. ± S.E.M. | Fibrillation min. ± S.E.M. |
|---|---|---|---|---|---|
| 0.9% NaCl solution | | 15 | 6.1 ± 0.27 | 8.3 ± 0.42 | 11.7 ± 0.45 |
| 9 | 0.5 | 3 | 7.2 ± 0.06 | 11.1 ± 0.68 | 14.6 ± 0.48 |
|  | 1.0 | 5 | 9.2 ± 0.10 | 15.3 ± 0.29 | 20.9 ± 0.50 |
|  | 2.0 | 5 | 13.2 ± 1.21 | 18.9 ± 0.13 | 24.6 ± 0.79 |
| 11 | 0.25 | 4 | 7.6 ± 0.24 | 11.3 ± 0.88 | 15.9 ± 0.49 |
|  | 0.5 | 5 | 9.9 ± 0.40 | 15.3 ± 0.52 | 19.1 ± 0.89 |
|  | 1.0 | 5 | 13.2 ± 1.29 | 19.3 ± 1.24 | 23.5 ± 0.42 |
| 19 | 1.0 | 6 | 6.6 ± 0.32 | 10.4 ± 2.58 | 15.1 ± 0.70 |
|  | 4.0 | 4 | 9.8 ± 0.34 | 16.1 ± 2.62 | 17.4 ± 1.22 |
|  | 8.0 | 4 | 13.8 ± 0.35 | 27.0 ± 1.10 | 30.6 ± 1.72 |
| 20 | 1.0 | 4 | 7.1 ± 0.49 | 12.3 ± 0.42 | 15.5 ± 0.59 |
|  | 2.0 | 4 | 9.2 ± 0.65 | 15.1 ± 0.22 | 19.5 ± 0.54 |
|  | 4.0 | 6 | 11.7 ± 0.50 | 18.4 ± 0.75 | 23.5 ± 1.63 |
| chinidin | 5.0 | 3 | 6.9 ± 0.06 | 10.4 ± 0.45 | 13.7 ± 0.44 |
|  | 10.0 | 5 | 8.4 ± 0.42 | 11.9 ± 0.64 | 15.8 ± 1.00 |
|  | 20.0 | 4 | 10.7 ± 0.58 | 15.7 ± 0.48 | 18.1 ± 0.22 |

TABLE III

Effective of aconitin arrhythmia with rats; acute toxicity value (confidence limits 95%) with controls treated with a physiological saline solution provided with an aconitin infusion of 5 micrograms per kg resulting after 6.1 minutes in a chamber extrasystol. The ED$_{125}$ and ED$_{150}$ values correspond to an infusion time of 7.6 and 9.2.

| Compound No. | ED$_{125}$ mg/kg i.v. | ED$_{150}$ mg/kg i.v. | LD$_{50}$ mg/kg i.v. |
|---|---|---|---|
| 9 | 0.6 (0.5–0.7) | 0.9 (0.8–1.0) | 11 (9–13) |
| 11 | 0.26 (0.23–0.31) | 0.39 (0.33–0.45) | 1.96 (1.53–2.51) |
| 19 | 1.53 (1.28–1.82) | 2.44 (2.04–2.91) | 53 (46–62) |
| 20. | 1.21 (1.01–1.44) | 1.91 (1.61–2.28) | 15 (13–28) |
| Chinidin | 6.75 (5.4–8.3) | 11.9 (9.6–14.8) | — |
| 6 | 5.4 (3.1–9.4) | 23.1 (13–39.9) | 63 (56–70) |

What is claimed is:

1. A compound of the Formula (IA)

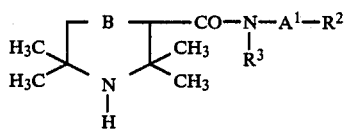

wherein
$A^1$ is a $C_1$ to $C_5$ straight or branched chain alkylene group;
B is a valence bond or a double bond;
$R^3$ is hydrogen or $C_1$ to $C_4$ alkyl; and
$R^2$ is unsubstituted amino or is a phenyl or phenoxy group unsubstituted or substituted by one or two $C_1$ to $C_4$ alkyl groups, $C_1$ to $C_4$ alkoxy groups, or halo substituents;
or a pharmaceutically acceptable acid addition salt thereof.

2. A compound of the Formula (IB)

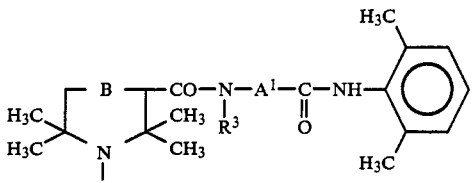

wherein
$A^1$ is a $C_1$ to $C_5$ straight or branched chain alkylene group;
B is a valence bond or a double bond;
$R^3$ is hydrogen or $C_1$ to $C_4$ alkyl; or a pharmaceutically acceptable acid addition salt thereof.

3. A compound of the Formula (IC)

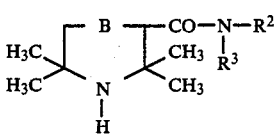

wherein
B is a valence bond or a double bond;
$R^3$ is hydrogen or $C_1$ to $C_4$ alkyl; and
$R^2$ is a diphenylmethyl, 4-pyridyl methyl, phenylamino, or 2,6-dimethylphenyl;
or a pharmaceutically acceptable acid addition salt thereof.

4. A compound selected from the group consisting of:
N-(2-hydroxy-3-amino-propyl)-2,2,5,5-tetramethyl-3-pyrroline-3-carboxamide, and
N-[(alpha-carbamoyl)-benzyl]-2,2,5,5-tetramethyl-3-pyrroline-3-carboxamide or a pharmaceutically acceptable acid addition salt thereof.

5. A method of treating arrhythmia in an animal subject which comprises the step of administering to said animal subject a therapeutically effective antiarrhythmic amount of a compound of the Formula (IA) as defined in claim 1 or a pharmaceutically acceptable acid addition salt thereof.

6. A method of treating arrhythmia in an animal subject which comprises the step of administering to said animal subject a therapeutically effective antiarrhythmic amount of a compound of the Formula (IB) as defined in claim 2 or a pharmaceutically acceptable acid addition salt thereof.

7. A method of treating arrhythmia in an animal subject which comprises the step of administering to said animal subject a therapeutically effective antiarrhythmic amount of a compound of the Formula (IC) as defined in claim 3 or a pharmaceutically acceptable acid addition salt thereof.

8. A method of treating arrhythmia in an animal subject which comprises the step of administering to said animal subject a therapeutically effective antiarrhythmic amount of a compound defined in claim 4 or a phrmaceutically acceptable acid addition salt thereof.

9. A compound of the Formula (ID)

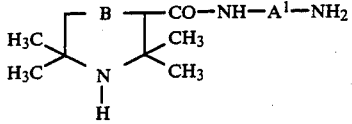

wherein $A^1$ is a $C_1$ to $C_5$ straight or branched chain alkylene group; and B is a valence bond or a double bond; or a pharmaceutically acceptable acid addition salt thereof.

10. The compound of the Formula (ID) defined in claim 9 selected from the group consisting of:
 (a) N-(3-aminopropyl)-2,2,5,5-tetramethylpyrrolidine-3-carboxamide;
 (b) N-(2-aminoethyl)-2,2,5,5-tetramethyl-2,5-dihydro-3-pyrroline-3-carboxamide;
 (c) N-(3-aminopropyl)-2,2,5,5-tetramethyl-2,5-dihydro-3-pyrroline-3-carboxamide;
 (d) N-(2-aminoisopropyl)-2,2,5,5-tetramethyl-2,5-dihydro-3-pyrroline-3-carboxamide;
 (e) N-(4-amino-n-butyl)-2,2,5,5-tetramethyl-2,5-dihydro-3-pyrroline-3-carboxamide; and
 (f) N-(2-amino-2-methyl-isopropyl)-2,2,5,5-tetramethyl-2,5-dihydro-3-pyrroline-3-carboxamide;
 or a pharmaceutically acceptable acid addition salt thereof.

11. A method of treating arrhythmia in an animal subject which comprises the step of administering to said animal subject a therapeutically effective antiarrhythmic amount of a compound defined in claim 9 or a pharmaceutically acceptable acid addition salt thereof.

12. A method of treating arrhythmia in an animal subject which comprises the step of administering to said animal subject a therapeutically effective antiarrhythmic amount of a compound defined in claim 10 or a pharmaceutically acceptable acid addition salt thereof.

13. 2-(2,2,5,5-tetramethyl-2,5-dihydro-3-pyrroline-3-carbonylamino)-N-(2,6-dimethyl-phenyl)-acetamide as defined in claim 2 or a pharmaceutically acceptable acid addition salt thereof.

14. N-(2,6-dimethyl-phenyl)-2,2,5,5-tetramethyl-2,5-dihydro-3-pyrroline-3-carboxamide as defined in claim 3 or a pharmaceutically acceptable salt thereof.

15. 2-(2,2,5,5-tetramethyl-2,5-dihydro-3-pyrroline-3-carbonylamino)-N-(2,6-dimethylphenyl)-propionamide as defined in claim 2 or a pharmaceutically acceptable acid addition salt thereof.

16. 2-[N-(2,2,5,5-tetramethyl-2,5-dihydro-3-pyrroline-3-carbonyl)]-3-(2,6-dimethyl-phenoxy)-aminopropane as defined in claim 1 or a pharmaceutically acceptable acid addition salt thereof.

17. 2-[N-(2,2,5,5-tetramethyl-3-pyrrolidine-3-carbonyl)]-3-(2,6-dimethyl-phenoxy)-aminopropane as defined in claim 1 or a pharmaceutically acceptable acid addition salt thereof.

18. 3-[N-(2,2,5,5-tetramethyl)-2,5-dihydro-3pyrroline]-carbonyl-diphenyl-methane amine as defined in claim 3 or a pharmaceutically acceptable acid addition salt thereof.

* * * * *